United States Patent
Miyanishi et al.

(10) Patent No.: US 6,896,896 B2
(45) Date of Patent: May 24, 2005

(54) PHYSIOLOGICALLY FUNCTIONAL FOODS OR COSMETICS CONTAINING SPHINGOGLYCOLIPIDS AND PROCESSES FOR THEIR PRODUCTION

(75) Inventors: Kenji Miyanishi, Uji (JP); Takahiro Ono, Uji (JP); Kazue Nawa, Uji (JP); Mayumi Hayashi, Uji (JP); Katsuyuki Mukai, Uji (JP)

(73) Assignee: Unitika Ltd., Hyogo (JP)

( * ) Notice: Subject to any disclaimer, the term of this patent is extended or adjusted under 35 U.S.C. 154(b) by 108 days.

(21) Appl. No.: 10/088,301

(22) PCT Filed: Jul. 17, 2001

(86) PCT No.: PCT/JP01/06182

§ 371 (c)(1),
(2), (4) Date: Mar. 18, 2002

(87) PCT Pub. No.: WO02/05662

PCT Pub. Date: Jan. 24, 2002

(65) Prior Publication Data

US 2003/0044449 A1 Mar. 6, 2003

(30) Foreign Application Priority Data

| Jul. 19, 2000 | (JP) | 2000-219087 |
| Jan. 30, 2001 | (JP) | 2001-021947 |
| Mar. 26, 2001 | (JP) | 2001-087695 |
| Jun. 21, 2001 | (JP) | 2001-188393 |

(51) Int. Cl.$^7$ ............................................. A61K 47/00
(52) U.S. Cl. ........................................................ 424/439
(58) Field of Search ................................ 424/439, 400, 424/401

(56) References Cited

U.S. PATENT DOCUMENTS 6,316,032 B1  11/2001  Kado et al.

FOREIGN PATENT DOCUMENTS

| EP | 0 969 079 A1 | 1/2000 |
| JP | 11-113530 | 4/1999 |
| JP | 11-113530 A * | 4/1999 |
| JP | 2000-139345 | 5/2000 |
| WO | WO 99/33939 A1 * | 7/1999 |

OTHER PUBLICATIONS

"Cosmesome CM–1", Q.P. Corporation, Oct. 1999.*
English translation of JPA 11–113530 (not including bibliographical data).
English translation Kawashima, Shokuhin to Youki, 1991, vol. 32, No. 5, 290–295 (not including translation of Figure and Photos).
Special Issue/Moisturizing mechanism, and novel research and development of moisturizing agents, Fragrance Journal 1995–1, pp. 81–89.
Hirotaka Shibuya, et al. "Sphingolipids and Glycerolipids. I. Chemical Structures and Inophoretic Activities of Soyacerebrosides I and II from Soybean" Chem. Phar. Bull. 38 (11) 2933–2938 (1990).
Yasuhiko Fujino, et al. "Molecular Species of Ceramide and Mon–, Di, Tri–, and Tetraglycosylceramide in Bran and Endosperm of Rice Grains" Agric. Biol. Che., 49(9), 2753–2762 (1985).
Masao Ohnishi, et al. "Sphingolipid Classes and Their Molecular Species in Wheat Flour" Agric. Biol. Chem., 49(12), 3609–3611, 1985.
International Search Report, Sep. 2001.

* cited by examiner

*Primary Examiner*—Thurman K. Page
*Assistant Examiner*—Retford Berko
(74) *Attorney, Agent, or Firm*—Sughrue Mion, PLLC

(57) ABSTRACT

The present invention relates to functional foods or cosmetics containing sphingoglycolipids and a process of producing the same.

9 Claims, No Drawings

PHYSIOLOGICALLY FUNCTIONAL FOODS OR COSMETICS CONTAINING SPHINGOGLYCOLIPIDS AND PROCESSES FOR THEIR PRODUCTION

TECHNICAL FIELD

This invention relates to functional foods and cosmetics containing sphingoglycolipids and a method of producing the same.

BACKGROUND ART

Recent researches have been revealing that some complex lipids, particularly some glycolipids exhibit pronounced physiological activities. For example, it has come to be known that ceramides composed of sphingosine and fatty acids and cerebrosides composed of sphingosine, sugar, and fatty acids are present in the stratum corneum of human skin and serve to prevent evaporation loss of water from the body. Application of the glycolipids to the cosmetics taking advantage of this high moisturizing activity and application to pharmaceuticals taking advantage of elastase inhibitory activity or free radical inhibitory activity have advanced.

Ceramide related substances typified by the sphingoglycolipids have been supplied as extract from bovine brain, etc. However, since the BSE (bovine spongiform encephalopathy) outbreak in 1986 the supply has decreased markedly because of the risk of human infection. The demand for safe ceramide related substances of plant origin has thus been increasing.

Seeing that ceramide related substances of plant origin are by no means inferior to those of animal origin and involve neither side effects nor toxicity as has recently been revealed, extraction of ceramide related substances from plant raw materials are now under intensive study. Sphingoglycolipids of plant origin, particularly glycosylceramides, that have hitherto been reported include those obtained from cereals and beans, such as rice (see *Agric. Biol. Chem.*, vol. 49, p. 2753 (1985)), rice bran (see JP-A-62-187404 and JP-A-11-279586), wheat (see *Agric. Biol. Chem.*, vol. 49, 1. 3609 (1985) and a published Japanese translation of a PCT patent application No. Hei.-6-507653), and soybeans (see *Chem. Pharm. Bull.*, vol. 38, No. 11, p. 2933 (1990)).

Ceramides have been added to skin care products, hair care products, bathing preparations, and the like so that the manner of taking in ceramides has been almost restricted to percutaneous absorption. In recent years, it has been reported that one-month administration of 20 mg/day of wheat extract containing 3 wt % of wheat ceramides results in improvement on skin's moisture retention (see *Fragrance Journal*, vol. 23, No. 1, p. 81 (1995)), and oral intake of ceramides in the form of eatable cosmetics has been attracting attention.

Cosmetics containing ceramides of animal (horse) origin, ceramides produced by yeast fermentation or synthetic ceramides are now commercially available. Being safe, ceramides of plant origin have a favorable image, and many cosmetics featuring the plant origin are on the market.

However, plants which have been so far utilized as materials for supplying plant sphingoglycolipids are limited to cereals and beans, of which the sphingoglycolipids content is not much, usually about 0.01% by weight. All of these plant materials are edible for human consumption, whereas residue after extracting sphingoglycolipids therefrom has no value as food. The problem of using plants lies in that a vast quantity of food materials lose their value as food only to provide a slight amount of sphingoglycolipids. Looking out over the food processing industry, on the other hand, it is noted that 3,000 to 4,000 tons of "tobiko" powder occurs a year as a by-product in making konjac products (devil's tongue) from konjac (elephant foot or *Amorphophallus konjac*). Tobiko powder finds no use as a food due to its peculiar acrid taste and irritating smell, except that part of tobiko powder is made use of as a fertilizer or a concrete thickener. Further, cotton seed oil cake, which is a by-product in squeezing cotton seed to obtain cotton seed oil, had been used as an animal feed rich in vegetable protein until 10 years ago. However, giving cow cotton seed as a high-energy feed is increasing among dairy farmers aiming to improve fat content in milk. Increase of utility of cotton seed oil cake is therefore demanded.

The present invention relates to functional foods and cosmetics containing sphingoglycolipids of plant origin which are attracting attention as a functional material of cosmetics and foods. It is an object of the present invention to provide functional foods and cosmetics made of materials of plant origin which are rid of the safety problem often pointed out in relation to the conventional materials extracted from animal tissue and yet find no value as food for the time being.

DISCLOSURE OF THE INVENTION

The present inventors have sought for plant raw materials containing sphingoglycolipids in a higher concentration than the conventionally used plant raw materials such as cereals and beans. As a result, they have unexpectedly found out that natural resources of plant origin, such as tuberous and corm vegetables (e.g., tobiko powder (fly powder) by-produced in making konjac (*Amorphophallus konjac*) products), and oil cakes (e.g., cotton seed oil cake), contain sphingoglycolipids in concentrations comparable to or higher than those in cereal and bean crops and completed the present invention. More specifically, they have found that tuberous and corm vegetables including sweet potato and white potato as well as konjac tobiko powder, which occurs in quantity in making konjac products and is of little utility value as food, and oil cakes such as cotton seed oil cake are rich in sphingoglycolipids, particularly cerebrosides; that these components can be extracted efficiently from the above-mentioned natural resources by using organic solvents; and that foods or cosmetics containing the extract exhibit higher moisture retaining action than those containing conventional sphingoglycolipids of plant (cereal) origin. The present invention has been reached based on these findings.

A first aspect of the invention consists in functional foods characterized by containing sphingoglycolipids derived from tuberous and corm vegetables, preferably konjac, or oil cakes.

A second aspect of the invention consists in functional foods containing sphingoglycolipids and plant sterols. Preferably the sphingoglycolipids are those extracted from tuberous and corm vegetables, particularly konjac, or oil cakes.

A third aspect of the invention resides in cosmetics characterized by containing sphingoglycolipids derived from tuberous and corm vegetables, preferably konjac, or oil cakes.

A fourth aspect of the invention lies in a method of producing sphingoglycolipids-containing products, functional foods or cosmetics characterized by comprising adding an organic solvent to a tuberous and corm vegetable or oil cake and extracting sphingoglycolipids.

BEST MODE FOR CARRYING OUT THE INVENTION

The present invention will be hereinafter described in detail.

The plants which can be used as raw materials in the present invention include any kind of tuberous and corm vegetables and oil cakes, such as sweet potato, white potato, taro, yam, konjac, long yam, cotton seed oil cake, rapeseed oil cake, coconut oil cake, and palm oil cake. They can be used either as such or after processed by drying, grinding, heating or a like operation. Preferred of them is konjac. Konjac tobiko powder is particularly preferred because it is to be discarded in quantity and is easily available.

The sphingoglycolipids which can be used in the invention can be obtained by, for example, extraction from the above-recited plant raw materials with an organic solvent as follows.

Any organic solvents can be used as an extracting solvent as long as they are not reactive on the raw material and sphingoglycolipids during extraction and do not impair the effects of the present invention. The solvents can be used either individually or as a mixture of two or more thereof. Such organic solvents include alcohols, such as methanol, ethanol, 1-propanol, 2-propanol, 1-butanol, 2-butanol, and tert-butanol; polyhydric alcohols, such as ethylene glycol, propylene glycol, butylene glycol, and glycerol; ketones, such as acetone and methyl ethyl ketone; esters, such as methyl acetate and ethyl acetate; ethers, such as tetrahydrofuran and diethyl ether; halogenated hydrocarbons, such as dichloromethane, dichloroethane, and chloroform; aliphatic hydrocarbons, such as hexane, pentane, and petroleum ether; aromatic hydrocarbons, such as toluene; polyethers, such as polyethylene glycol; and pyridines. Preferred of them are methanol, ethanol, acetone, and hexane. Methanol and ethanol are particularly preferred. In using these polar organic solvents for extraction, extraction efficiency may be improved by addition of water, additives such as surface active agents, and the like in amounts that do not impair the effects of the invention.

The amount of the organic solvent used for extraction is desirably about 1 to 30 times, particularly about 1 to 10 times, the plant raw material. With the amount of the organic solvent being not smaller than this range, distribution of the solvent throughout the raw material is ensured to achieve sufficient extraction. Use of a greater amount of the solvent than this range results in no more improvement in extractability. The amount of the solvent falling within this range minimizes the load of solvent removal in the subsequent concentration step.

The extracting temperature depends on the boiling point of the solvent. In the case of methanol or ethanol, a suitable temperature is from room temperature up to 70° C., preferably from about room temperature to 60° C. At temperatures not lower than room temperature, the extraction efficiency can be increased. Raising the temperature over the above range is not so influential on extraction efficiency. Energy consumption can be reduced at temperatures not higher than the above range.

The extracting time is 10 minutes to 24 hours, preferably 1 to 10 hours. The extracting time being not shorter than 10 minutes, extraction can be carried out more sufficiently. Since an increase of extractability is not expected with a longer time than 24 hours, the above time range ensures completion of extraction in a minimized time.

The extraction operation is not limited to a single batch operation. A fresh solvent may be added to the raffinate to repeat extraction, or an extracting solvent may be brought into contact with the feed a plurality of times. That is, the extraction operation can be carried out in any of a batch process, a semi-continuous process, and a countercurrent multistage process. Known extraction processes such as Soxhlet extraction may be used.

The extraction residue is then separated. Methods of separation are not particularly limited. Known methods, such as filtration by suction, pressure filtration using a filter press or a cylinder press, decantation, centrifugation, and centrifugal filtration, can be employed.

The extract thus obtained is preferably sent to a concentration step. The method of concentration is not particularly limited. For example, the extract is concentrated by means of a vacuum concentration apparatus, such as an evaporator, or a centrifugal thin film evaporator, such as Evapol (from Ohkawara Seisakusho) or by heating to remove the solvent.

The resulting concentrate can be used as such or, if necessary, be purified in a conventional manner to remove impurities and increase the purity. Useful purification procedures include washing with water, washing with hexane, passing through a silica gel column, a resin column, a reversed-phase column, etc., partitioning between solvents having different polarities, and recrystallization. Where obtaining highly pure sphingoglycolipids is particularly needed, purification is preferably conducted by treating the concentrate with an alkaline solution, partitioning with chloroform, diethyl ether, etc., collecting and concentrating the organic layer, and separating the sphingoglycolipids by column chromatography on silica gel.

The sphingoglycolipids in the resulting concentrate are analyzed most conveniently by thin layer chromatography using commercially available sphingoglycolipids, especially glucosylceramide as a standard. The concentrate is applied on a silica gel thin layer plate and developed with an appropriate solvent system, such as a chloroform-methanol system. Visualization of the spots by color development with concentrated sulfuric acid or an anthrone reagent makes it easy to judge the presence of sphingoglycolipids in the concentrate in a high concentration. Presence of sphingoglycolipids in abundance can also be ascertained by other conventional techniques, such as high-performance liquid chromatography and various chromatography/mass spectrometries.

The functional foods as referred to herein are preparations which can be orally taken to exert one or more than one effects selected from skin moisture retention, improvement on skin roughening, skin beautification, and treatment of atopic dermatitis, allergic dermatitis, psoriasis, pimples, skin aging, hair loss, cancers, AIDS, hypertension, cholesterolemia, arteriosclerosis, and so on. The concentrate may be taken directly as a functional food of the present invention but, for easy handling, is preferably mixed with carriers and/or diluents acceptable as food and drink additives and formed into preparation forms, such as powders, tablets, capsules, gels, aqueous dispersions, ethanolic solutions or edible oil solutions.

Carriers which can be preferably used in powders, tablets or capsules include dextrin, cyclodextrins, potato starch, corn starch, and lactose. Carriers useful in gels include gelatin, agar, guar gum, gum arabic, and konjac mannan. Water for use in aqueous dispersions is not limited. Water from springs or deep sea water may be used. The aqueous dispersions can contain saccharides, amino acids, and inorganic salts as far as the present invention is not ruined. Fruit juice or carbonated water is also useful. An emulsifier is preferably added to the aqueous dispersion to help the concentrate be effectively dispersed. Useful emulsifiers include sucrose fatty acid esters, glycerol fatty acid esters, polyglycerol fatty acid esters, propylene glycol fatty acid esters, and soybean lecithin. Ethanol to be used in the ethanolic solutions is preferably distilled alcohol. The concentration of ethanolic solutions is not particularly limited. The edible oils to be used in the edible oil solutions are not particularly limited and include soybean oil, rapeseed oil, olive oil, sesame oil, safflower oil, and wheat germ oil. In order to effectively disperse the concentrate of the invention in edible oil, an emulsifier can be added. Suitable emulsifiers include soybean lecithin, sucrose fatty acid esters, glycerol fatty acid esters, polyglycerol fatty acid esters, and propylene glycol fatty acid esters.

The functional foods having the above-described preparation forms can be orally taken alone or as mixed into foods and/or beverages. The foods and/or beverages are not particularly limited and include, for example, staple foods such as bread, wheat noodle, buckwheat noodle, and rice; confectionery, such as cookies, cake, jelly, pudding, candy, chewing gum, and yogurt; liquors; and beverages, such as soft drinks, nutritious drinks, coffee, tea, and milk. In order to promote the effects, the mixed foods can further contain vitamins, collagen, squalane, soybean lecithin, plant sterols, hyaluronic acid, sorbitol, chitin, chitosan, glucosamine, niacin, niacinamide, Centella asiatica extract, polyphenols, co-enzyme Q10, pycnojenol, deep sea water, and the like. In particular, addition of plant sterols is preferred for producing high effects on skin moisture retention, atopic dermatitis, etc.

Any kind of plant sterols extracted from plants can be used in the invention. Specifically, waste such as deodorized scum oil occurring in production of oil, e.g., rice bran oil, cotton seed oil or soybean oil can be used. They are also extractable from konjac tobiko powder or the waste from cane sugar factories. β-Sitosterol, campesterol, stigmasterol, sitostanol, campestanol, stigmastanol, and derivatives thereof can be used either individually or as a mixture of two or more thereof. Any derivatives, either synthesized or naturally-occurring, can be used unless they impair the effects of the invention. Sterol glycosides having sugar bonded, esterified compounds, and compounds having an amide linkage are preferred.

The plant sterols used in the invention can be obtained by known processes. A typical process comprises alkali treatment of deodorized scum oil which is by-produced in the deodorization step of soybean oil by steam distillation, extraction with an organic solvent, e.g., hexane, and crystallization from a poor solvent, e.g., acetone.

Commercially available plant sterols for foods as supplied by Eisai Co., Ltd. (trade name: Phytosterol F), Tuno Food Industrial Co., Ltd., etc. are also employable in the present invention.

Where plant sterols are taken in combination with sphingoglycolipids according to the present invention, the sphingoglycolipids to be combined may be any of synthetic products, fermentation products, and products of animal or plant origin. From the standpoint of use as a food, those of plant origin which are of high safety and have been eaten are preferred. Any sphingoglycolipids of plant origin can be used as far as they are extracted from edible plants. Preferred are those extracted from cereal crops, such as wheat, wheat bran, barley, rice, rice bran, and corn; beans, such as soybeans; greens, such as spinach, komatuna, and boy choy; tuberous and corm vegetables, such as sweet potato, white potato, taro, yam, konjac, and long yam; and oil cakes, such as cotton seed oil cake, rapeseed oil cake, coconut oil cake, and palm oil cake. Those extracted from the tuberous and corm vegetables or oil cakes are still preferred. In particular, sphingoglycolipids extracted from konjac are the most preferred for their high effects.

Where sphingoglycolipids and plant sterols are mixed into other foods and/or beverages, their contents in the mixtures vary according to the food or food intake and cannot be generally specified but may be represented in terms of their intakes. An advisable daily intake of sphingoglycolipids is 1 µg to 100 g, and an advisable daily intake of plant sterols is 1 mg to 1000 g. The contents in foods are adjusted so as to give such levels of intake.

The material containing sphingoglycolipids extracted from plants can be powdered by drying by lyophilization, spray drying, vacuum drying or a like technique. If necessary, the dried product is ground in a sample mill, a speed mill, a blender, a mixer, etc. The resulting powder may sometimes exhibit viscosity. In such cases, carriers capable of accelerating powderization can be added to such an extent that would not damage the effects of the invention. Such carriers include corn starch, potato starch, dextrin, cyclodextrins, wheat flour, bread crumbs, edible salt, zeolite, talc, and oyster shell powder.

Tablets are prepared by putting the powder preparation obtained as described above in a tablet machine and punching into tablets. A binder may be used in such an amount that does not impair the effects of the invention.

Capsules are prepared by putting the powder preparation obtained as described above and/or a solution preparation into capsules for medicines or foods. Any capsules can be used unless the effects of the invention are impaired.

Gels are prepared by any known technique as long as the effects of the present invention are not ruined. For example, the resulting sphingoglycolipids-containing product is dispersed and/or dissolved in water, and a conventionally known gelling agent, thickening polysaccharide, etc. is added thereto. Gelling agents used for foods, such as gelatin and agar, are used preferably.

Aqueous dispersions are prepared by stirring the sphingoglycolipids-containing product in a prescribed amount of water. Dispersing may be accelerated by subjecting the system to ultrasonication or adding a known emulsifier or dispersant as long as the effects of the present invention are not damaged.

Soluble in ethanol, the sphingoglycolipids-containing product is simply dissolved in ethanol to give an ethanolic solution. If desired, a stabilizer may be added to the ethanolic solution to prevent precipitation or turbidity within such an amount that does not impair the effects of the invention.

Soluble in edible oils, the sphingoglycolipids-containing product can be directly dissolved in edible oils to provide edible oil solutions. Where difficult to dissolve, the sphingoglycolipids-containing product is once dissolved in a small amount of soybean lecithin or egg yolk lecithin and then dissolved in an edible oil to prepare an edible oil solution with ease. In order to prevent precipitation or turbidity, a stabilizer, etc. may be added within such an amount that does not impair the effects of the invention. Further, dissolving can be accelerated by slightly heating the system to reduce the viscosity of the edible oil.

The edible oils which can be used in the functional foods of the invention are not particularly limited. Useful edible oils include animal fats and oils, such as lard, beef tallow, whale oil, fish oil, and butter; vegetable oils, such as rapeseed oil, soybean oil, olive oil, rice oil, sunflower oil, and coconut oil; and functionalized synthetic oils or mixed oils. They can be used either individually or as a mixture of two or more thereof. Preferred of them are vegetable oils and health-friendly synthetic oils.

Made up of components of plant origin, the functional foods according to the present invention have high safety. Therefore, the oral intake and the interval of intake are not particularly limited. An advisable daily intake for manifestation of the aimed effects of the invention is from 1 μg to 100 g in terms of the sphingoglycolipids content. It is recommended to maintain taking at a frequency of ten times a day to once per three days. It is advisable to continue taking for at least 7 days, preferably 14 days or longer.

The cosmetics as referred to in the present invention include preparations which, when applied to the skin or hair, penetrate inside to exert one or more than one effects selected from skin moisture retention, skin whitening, improvements on wrinkles, dark blotches, freckles, and skin roughening, hair growth, prevention of hair splitting, and treatment of atopic dermatitis, allergic dermatitis, pimples, xeroderma, and the like. Accordingly, the present invention embraces in its scope a method for treating and/or preventing these symptoms which comprises applying the sphingoglycolipids of the invention in an amount effective on treatment and/or prevention of these symptoms. The formula may solely comprise the sphingoglycolipids or be a combination with other cosmetic materials, i.e., cosmetically acceptable carriers and/or diluents.

Cosmetically acceptable carriers and/or diluents are not particularly limited. Examples include colorants, such as titanium mica, talc, silica, and titanium dioxide; oily materials, such as olive oil, castor oil, jojoba oil, bees wax, lanolin, squalane, cetanol, liquid paraffin, methylpolysiloxane, silicone polyether copolymers, and behenyl alcohol; humectants, such as glycerol, hyaluronic acid, sorbitol, propylene glycol, dipropylene glycol, chitin, and chitosan; surface active agents, such as alkylsulfates and alkyl ether sulfates; emulsifiers, such as sucrose fatty acid esters, polyglycerol fatty acid esters, sorbitan fatty acid esters, lecithin, polyoxyethylene alkyl ethers, and alkyl glucosides; vegetable gum or water-soluble polymers, such as quince seed gum, xanthan gum, sodium carboxymethyl cellulose (CMC), carboxyvinyl polymers, polyvinylpyrrolidone, and polyvinyl alcohol; water; and ethanol.

The form is not restricted. For example, the cosmetics can be applied to the skin in the form of lotions, emulsions, moisture creams, sunscreens, anti-sunburn cosmetics, face packs, foundations, finishing powders, rouge, eye make-ups, perfumes, eau-de-colognes, lip creams, lipsticks, etc.; or to the hair in the form of hair growth products, pomade, setting lotions, hair sprays, hair dyes, hair tonics, eyelash cosmetics, etc. The formula can be added to facial cleansing creams, facial soaps, shampoos, hair conditioners, hair treatments, bathing preparations, and the like.

The method for extracting sphingoglycolipids to be incorporated into the cosmetics of the invention is the same as for extracting sphingoglycolipids to be incorporated into the functional foods. The sphingoglycolipids as extracted may be applied directly as cosmetics of the invention. For easier handling, the extract is dissolved in an organic solvent such as ethanol or dispersed in water.

Soluble in ethanol, the sphingoglycolipids-containing product is simply dissolved in ethanol to give an ethanolic solution. A stabilizer may be added to the solution to prevent precipitation or turbidity within such an amount that does not impair the effects of the invention.

The aqueous dispersion is prepared by stirring the sphingoglycolipids-containing product in a prescribed amount of water. Dispersing may be accelerated by subjecting the system to heat treatment or ultrasonication or adding a known emulsifier or dispersant as long as the effects of the present invention are not damaged. In particular, it is preferred that the sphingoglycolipids-containing product be once dissolved in an emulsifier, such as soybean or egg yolk lecithin, hydrogenated lecithin and then dispersed in water.

In order to enhance the effects, the cosmetics of the invention can further contain vitamins, collagen, squalane, soybean lecithin, plant sterols, hyaluronic acid, sorbitol, chitin, chitosan, glycerol, butylene glycol, propylene glycol, niacin, niacinamide, galactosylceramide, and so forth.

Containing the sphingoglycolipids derived from tuberous and corm vegetables or oil cakes, the cosmetics according to the present invention are of high safety and may have an unlimited sphingoglycolipids content. An advisable content of the sphingoglycolipids from tuberous and corm vegetables or oil-cakes for manifestation of the aimed effects of the invention is from 0.001% by weight to 100% by weight. At a content not smaller than 0.001 wt %, the effects of the invention show up sooner and more sufficiently.

The typical effects produced when the functional foods or cosmetics of the invention are taken orally or applied to the skin are enhancement of skin moisture retention and improvement on skin roughening. With respect to the skin moisture retention, the effect can be ascertained through known means such as measurement of transepidermal water loss (TEWL) or measurement of water content of the stratum corneum (hereinafter referred to as an SC water content). TEWL measurement can be made with, for example, Evaporimeter from Servo Med, Sweden or Tewameter from Courage+Khazaka Electronic GmbH, German. Measurement of the SC water content can be taken with, for example, Corneometer from Courage+Khazaka, German or Skikon 200 from IBS. The effect on improvement of skin roughening can be seen by observation with the naked eye and by the user's own feel. The skin whitening effect can also be seen by observation with the naked eye or quantitatively measured with a skin color meter Mexameter MX16 from Courage+Khazaka, German.

The effects produced by the functional foods or cosmetics of the invention orally taken or applied to the skin owe to the specific actions on the skin of the sphingoglycolipids contained in tuberous and corm vegetables or oil cakes. Therefore, the functional foods and cosmetics of the invention are superior to those containing the sphingoglycolipids obtained from conventional plant materials, such as wheat, rice bran, and soybeans, particularly in improving effects on skin roughening, atopic dermatitis, allergic dermatitis, and pimples.

EXAMPLES

The present invention will now be illustrated in greater detail with reference to Examples, but the present invention is not deemed to be limited thereto. To begin with, the measuring apparatus and methods used in Examples are described.

(1) Qualification of Sphingoglycolipids

Sphingoglycolipids were qualitatively analyzed by silica gel thin layer chromatography (TLC). A prescribed amount of a sample was applied to a silica gel plate (Silicagel 60F254 Type from Merc; layer thickness: 0.5 mm), and the plate was placed in a developing chamber containing chloroform:methanol:water (=87:13:2 by volume) to develop the sample. After the development, the silica gel plate was dried with a drier, etc., and sulfuric acid was sprayed thereto followed by heating to cause color development.

(2) Quantification of Sphingoglycolipids

Sphingoglycolipids were quantitatively analyzed by high-performance liquid chromatography (HPLC). HPLC was carried out by using LC Module 1 (from Waters Corp.), a column Inertsil SIL 100A (from GL Science Inc.), and chloroform:methanol (=9:1 by volume) as a solvent. The measurement was carried out at a flow rate of 1.0 ml/min at 37° C. A scattered light detector 500 ELSD from Alltech Associates Inc. was used for detection.

(3) Measurement of Stratus Corneum (SC) Water Content

Corneometer CM825 from Courage+Khazaka was used for SC water content measurement. Measurement was always made on the same site 1 cm below the left eye. Measurement was taken 10 times for each test person to obtain an average value, which was taken as the datum of that person, and the SC water content was represented as an average of the data from all test persons.

Example 1

Extraction of Sphingoglycolipids from Konjac Tobiko Powder

One kilogram of konjac tobiko powder was put into a stirring tank, and 2 liters of ethanol was added, followed by stirring at room temperature for 2 hours. The mixture was filtered to separate into an extract and a residue. The extract was concentrated in an evaporator to give 10.7 g of a brown waxy concentrate. The product was analyzed by the above-described methods for qualification and quantification. TLC revealed spots corresponding to sphingoglycolipids. The amount of the sphingoglycolipids in the extract was found to be 0.55 g by HPLC. The purity of the sphingoglycolipids in the tobiko powder extract was found to be 5.1 wt %.

Example 2

Extraction of Sphingoglycolipids from Cotton Seed Oil Cake

One kilogram of cotton seed oil cake was put into a stirring tank, and 2 liters of ethanol was added, followed by stirring at room temperature for 5 hours. The mixture was filtered to separate into an extract and a residue. The extract was concentrated in an evaporator to give 8.4 g of a brown waxy concentrate. The product was analyzed by the above-described methods for qualification and quantification. TLC revealed spots corresponding to sphingoglycolipids. The amount of the sphingoglycolipids in the extract was found to be 0.41 g by HPLC. The purity of the sphingoglycolipids in the cotton seed oil cake extract was found to be 4.9 wt %.

Example 3

Extraction of Sphingoglycolipids from Potato Peel

One kilogram of potato peel grinds (100 μm or smaller particles) was put into a stirring tank, and 2 liters of ethanol was added, followed by stirring at room temperature for 2 hours. The mixture was filtered to separate into an extract and a residue. The extract was concentrated in an evaporator to give 10.2 g of a yellow waxy concentrate. The product was analyzed by the above-described methods for qualification and quantification. TLC revealed spots corresponding to sphingoglycolipids. The amount of the sphingoglycolipids in the extract was found to be 0.42 g by HPLC. The purity of the sphingoglycolipids in the potato peel extract was 4.1 wt %.

Comparative Example 1

Extraction of Sphingoglycolipids from Wheat Flour

One kilogram of wheat flour was put into a stirring tank, and 2 liters of ethanol was added, followed by stirring at room temperature for 5 hours. The mixture was filtered to separate into an extract and a residue. The extract was concentrated in an evaporator to give 6.8 g of a deep yellowish brown waxy concentrate. The product was analyzed by the above-described methods for qualification and quantification. The spots of sphingoglycolipids appearing in TLC were light in color. The amount of the sphingoglycolipids in the extract was found to be 0.05 g by HPLC. The purity of the sphingoglycolipids in the wheat flour extract was as low as 0.7 wt %.

Comparative Example 2

Extraction of Sphingoglycolipids from Rice Bran

One kilogram of defatted rice bran was put into a stirring tank, and 3 liters of ethanol was added, followed by stirring at room temperature for 2 hours. The mixture was filtered to separate into an extract and a residue. The extract was concentrated in an evaporator to give 22.3 g of a brown waxy concentrate. The product was analyzed by the above-described methods for qualification and quantification. As a result of TLC, the spots of sphingoglycolipids appearing in TLC were light in color, while the spots corresponding to glyceroglycolipids, sterols, etc. developed deep colors. The amount of the sphingoglycolipids in the extract was found to be 0.38 g by HPLC. The purity of the sphingoglycolipids in the defatted rice bran extract was 1.7 wt %.

As described above, the content of sphingoglycolipid components in the tobiko powder extract obtained by using an organic solvent is as high as 5.1 wt % based on the extract and 0.055 wt % based on the feed. It has now been proved that sphingoglycolipid components are present in a tobiko powder extract in extremely high concentration and purity. It is also seen that sphingoglycolipid components are present in a potato peel extract and a cotton seed oil cake extract in sufficiently high concentration and purity as compared with the conventionally employed feeds for extraction, i.e., wheat flour and rice bran. Thus, the present invention is successful in recovering sphingoglycolipids from tuberous and corm vegetables and oil cakes in extremely high concentrations.

Example 4

Preparation of Powdered Functional Food

In 20.0 g of ethanol was dissolved 10.0 g of the konjac tobiko powder extract obtained in Example 1, and the solution was introduced into 200 g of water while stirring. The mixture was further stirred while in a dispersed state. Thirty minutes later, 5.0 g of sodium chloride was added, and the stirring was continued for an additional 10 minute period to give a brown precipitate, which weighed 6.8 g. The sphingoglycolipids content was 0.45 g as measured by HPLC. The extract was washed with water to have the sphingoglycolipids purity increased to 6.6 wt %. The washing operation was repeated once more to give 6.4 g of a precipitate (designated precipitate A) containing sphingoglycolipids of konjac tobiko powder origin. The sphingoglycolipids content was found to be 0.44 g as a result of HPLC. The purity of the sphingoglycolipids increased up to 6.9 wt % by washing twice.

In 15 ml of ethanol was dissolved 5.0 g of precipitate A, and the resulting ethanolic solution was poured into a suspension of 15.0 g of corn starch in 50 ml of water while stirring, and the suspension was heated in a boiling water bath for 5 minutes while stirring. As the corn starch was dissolved and swollen, the suspension increased its viscosity and became pasty. The resulting pasty composition was dried in a vacuum drier at 50° C. for 12 hours to give a milky white solid, which was ground in a blender to obtain 19.3 g of a powdered functional food containing sphingoglycolipids of konjac tobiko powder origin. The resulting powder was soaked in ethanol, and the soluble components thus dissolved out were analyzed by TLC. Spots of sphingoglycolipids were clearly observed.

Example 5

Preparation of Powdered Functional Food

In 15 ml of ethanol was dissolved 5.0 g of precipitate A of Example 4. The resulting ethanolic solution was poured into a suspension of 10.0 g of β-cyclodextrin in 20 ml of water while stirring. As stirring was continued, the suspension increased its viscosity and became pasty. The resulting pasty composition was dried in a vacuum drier at 50° C. for 12 hours to give a milky white solid, which was ground in a blender to obtain 14.8 g of a powdered functional food containing sphingoglycolipids of konjac tobiko powder origin. The resulting powder was soaked in ethanol, and the soluble components thus dissolved out were analyzed by TLC. Spots of sphingoglycolipids were clearly observed.

Example 6

Preparation of Powdered Functional Food

In 15 ml of ethanol was dissolved 5.0 g of precipitate A of Example 4. The resulting ethanolic solution was poured into a suspension of 15.0 g of corn starch in 50 ml of water while stirring, and the suspension was heated in a boiling water bath for 5 minutes while stirring. As the corn starch was dissolved and swollen, the suspension increased its viscosity and became pasty. To the resulting pasty composition was added 450 ml of water, followed by stirring to obtain a low-viscosity dispersion. The dispersion was delivered to a spray drier (Spray Dryer LT-8, manufactured by Ohkawara Kakoki K.K.) at a rate of 3 1/min and powdered under conditions of an inlet temperature of 250° C., an outlet temperature of 150° C., and an atomizer revolution speed of 35000 rpm. The resulting powdered functional food containing sphingoglycolipids of konjac tobiko powder origin weighed 18.7 g and assumed a light brown color. The resulting powder was soaked in ethanol, and the soluble components thus dissolved out were analyzed by TLC. Spots of sphingoglycolipids were clearly observed.

Example 7

Preparation of Functional Food in Aqueous Dispersion Form

In 500 ml of water were put 5.0 g of precipitate A of Example 4 and 2.5 g of decaglycerol monostearate (SY Glyster MSW-750, available from Sakamoto Yakuhin Kogyo Co., Ltd.) and dispersed by ultrasonication using BRANSON 3200, available from Yamato Scientific Co., Ltd., for 30 minutes. There was obtained a functional food of aqueous dispersion form containing sphingoglycolipids of konjac tobiko powder origin. The resulting aqueous dispersion was uniform and generated no sediment on 3 months' standing.

Example 8

Preparation of Gelatinous Functional Food

In 15 ml of ethanol was dissolved 5.0 g of precipitate A of Example 4. The resulting ethanolic solution was poured into a solution of 15.0 g of gelatin in 20 ml of water heated at 60° C. while stirring. The solution was allowed to cool to room temperature whereupon it turned into an ocherous hard gel. There was thus obtained a gelatinous functional food containing sphingoglycolipids of konjac tobiko powder origin.

Comparative Example 3

Preparation of Food Containing Sphingoglycolipids of Wheat Flour Origin

In 10.0 g of ethanol was dissolved 5.0 g of the wheat flour extract obtained in Comparative Example 1, and the solution was introduced into 100 g of water while stirring. The mixture was further stirred while in a dispersed state. Thirty minutes later, 2.5 g of sodium chloride was added, and the stirring was continued for an additional 10 minute period to give a brown precipitate, which weighed 3.6 g. The sphingoglycolipids content was 0.04 g as measured by HPLC. After washing with water, the extract had a sphingoglycolipids purity of 1.1 wt %. The washing operation was repeated once more to give 3.4 g of a precipitate containing sphingoglycolipids of wheat flour origin. The sphingoglycolipids content was found to be 0.04 g as a result of HPLC. The purity of the sphingoglycolipids obtained after washing twice was 1.2 wt %.

In 300 ml of water were put 3.0 g of the precipitate and 1.5 g of decaglycerol monostearate (SY Glyster MSW-750, available from Sakamoto Yakuhin Kogyo Co., Ltd.), and the mixture was treated in the same manner as in Example 7 to obtain an aqueous dispersion containing sphingoglycolipids of wheat flour origin.

Comparative Example 4

Preparation of Food Containing Sphingoglycolipids of Rice Bran Origin

In 20.0 g of ethanol was dissolved 10.0 g of the rice bran extract obtained in Comparative Example 2, and the solution was introduced into 200 g of water while stirring. The mixture was further stirred while in a dispersed state. Thirty minutes later, 5.0 g of sodium chloride was added, and the stirring was continued for 10 minutes to give a brown precipitate, which weighed 7.4 g. The sphingoglycolipids content was 0.24 g as measured by HPLC. After washing with water, the extract had a sphingoglycolipids purity of 3.2 wt %. The washing operation was repeated once more to give 6.9 g of a precipitate containing sphingoglycolipids of rice bran origin. The sphingoglycolipids content was found to be 0.22 g as a result of HPLC. The purity of the sphingoglycolipids obtained after washing twice was 3.2 wt %.

In 300 ml of water were put 3.0 g of the precipitate and 1.5 g of decaglycerol monostearate (SY Glyster MSW-750, available from Sakamoto Yakuhin Kogyo Co., Ltd.), and the mixture was treated in the same manner as in Example 7 to obtain an aqueous dispersion containing sphingoglycolipids of rice bran origin.

Test Example 1

Influences on SC Water Content

The functional food of the present invention obtained in Example 7 (aqueous dispersion), the aqueous dispersions obtained in Comparative Examples 3 and 4, and a dispersion containing no sphingoglycolipids were tested for SC water content improving effects on ten volunteers for each sex (five persons between the ages of 20 and 40 and five persons between the ages of 40 and 60 for each sex). The dispersion containing no sphingoglycolipids was prepared by dissolving 1.5 g of decaglycerol monostearate (SY Glyster MSW-750, available from Sakamoto Yakuhin Kogyo Co., Ltd.) in 300 ml of water.

The test persons were asked to take in 1.45 ml/day of the functional food of the invention, 8.5 ml/day of the dispersion obtained in Comparative Example 3, and 3.25 ml/day of the dispersion obtained in Comparative Example 4 each for 30 days. These daily intakes correspond to 1 mg of the sphingoglycolipids per day. The dispersion containing no sphingoglycolipids as a control was taken in an amount of 1.45 ml/day.

The SC water content of the skin 1 cm below the left eye was measured with Corneometer after 10 days, 20 days and 30 days from the first day of taking. The average results of the twenty test persons are shown in Table 1.

TABLE 1

|  | Initial Value | After 10 Days | After 20 Days | After 30 Days |
| --- | --- | --- | --- | --- |
| Example 7 (tobiko powder origin) | 44 | 62 | 68 | 73 |
| Comparative Example 3 (wheat flour origin) | 47 | 51 | 55 | 58 |
| Comparative Example 4 (rice bran origin) | 46 | 49 | 53 | 60 |
| Control | 43 | 45 | 47 | 46 |

It is seen from Table 1 that taking sphingoglycolipids of konjac tobiko powder origin produces greater effects in improving the skin SC water content than taking sphingoglycolipids of wheat flour or rice bran origin.

Test Example 2

Improving Effect on Skin Roughening

The functional food of the present invention obtained in Example 7 (aqueous dispersion), the aqueous dispersions obtained in Comparative Examples 3 and 4, and a dispersion containing no sphingoglycolipids were tested for rough skin improving effects with cooperation of ten females suffering from skin roughening on the back of their hands. The dispersion containing no sphingoglycolipids was prepared by dissolving 1.5 g of decaglycerol monostearate (SY Glyster MSW-750, available from Sakamoto Yakuhin Kogyo Co., Ltd.) in 300 ml of water.

The test persons were asked to take in 1.45 ml/day of the functional food of the invention, 8.5 ml/day of the dispersion obtained in Comparative Example 3, and 3.25 ml/day of the dispersion obtained in Comparative Example 4 each for 15 days. These daily intakes correspond to 1 mg of the sphingoglycolipids per day. The dispersion containing no sphingoglycolipids as a control was taken in an amount of 1.45 ml/day.

Meanwhile they were asked to answer a questionnaire about the condition of the back of their hands after 5 days, 10 days and 15 days. The results obtained are shown in Table 2 as a total score.

TABLE 2

|  | After 5 Days | After 10 Days | After 15 Days |
| --- | --- | --- | --- |
| Example 7 (tobiko powder origin) | 22 | 29 | 34 |
| Comparative Example 3 (wheat flour origin) | 19 | 22 | 29 |
| Comparative Example 4 (rice bran origin) | 18 | 22 | 27 |
| Control | 8 | 13 | 14 |

Answers and Scores:
4 . . . The skin roughening was completely healed.
3 . . . The skin condition was improved greatly.
2 . . . The skin condition was improved.
1 . . . The skin condition was unchanged.
0 . . . The skin condition got worse.

It is seen from Table 2 that taking sphingoglycolipids of konjac tobiko powder origin brings about more excellent effects of improving skin roughening than taking sphingoglycolipids of wheat flour or rice bran origin.

Example 9

Preparation of Powdered Functional Food Containing Plant Sterols

Plant sterols of soybean oil origin which mainly comprise β-sitosterol (2.0 g; Phytosterol F from Eisai Co., Ltd., hereinafter referred simply to as Phytosterol F) was added to 14.8 g of the powder containing sphingoglycolipids of konjac tobiko powder origin obtained in Example 5, and the mixture was stirred well to get uniform to prepare a powdered functional food.

Example 10

Preparation of Plant Sterols-Containing Functional Food of Aqueous Dispersion Form Precipitate A of Example 4 (5.0 g) and 2.0 g of Phytosterol F were kneaded at 50° C. for 5 minutes to obtain a brown paste. The paste was put into 500 ml of water together with 2.5 g of decaglycerol monostearate (SY Glyster MSW-750, available from Sakamoto Yakuhin Kogyo Co., Ltd.) and dispersed by ultrasonication using BRANSON 3200, available from Yamato Scientific Co., Ltd., for 30 minutes. The resulting aqueous dispersion containing sphingoglycolipids and plant sterols was uniform and formed no sediment on 3 months' standing.

Example 11

Preparation of Plant Sterols-Containing Functional Food of Aqueous Dispersion Form Precipitate A of Example 4 (1.0 g) and 2.0 g of Phytosterol F were kneaded at 50° C. for 5 minutes to obtain a brown paste. The paste was put into 500 ml of water together with 2.5 g of decaglycerol monostearate (SY Glyster MSW-750, available from Sakamoto Yakuhin Kogyo Co., Ltd.) and dispersed by ultrasonication using BRANSON 3200, available from Yamato Scientific Co., Ltd., for 30 minutes. The resulting aqueous dispersion containing sphingoglycolipids and plant sterols was uniform and generated no sediment on 3 months' standing.

Example 12

Preparation of Plant Sterols-Containing Functional Food of Aqueous Dispersion Form An aqueous dispersion containing sphingoglycolipids and plant sterols was prepared in the same manner as in Example 10, except for replacing Phytosterol F with β-sitostanol (from Sigma). The resulting aqueous dispersion containing sphingoglycolipids and plant sterols was uniform and generated no sediment on 3 months' standing.

Example 13

Preparation of Plant Sterols-Containing Gelatinous Functional Food

In 15 ml of ethanol was dissolved 5.0 g of precipitate A of Example 4, and 2.0 g of Phytosterol F was added thereto, followed by stirring at 30° C. for 5 minutes to obtain a solution. The resulting ethanolic solution was introduced into an aqueous solution of 15.0 g of gelatin in 20 ml of water heated at 60° C. while stirring. The solution was allowed to cool to room temperature whereupon it turned into an ocherous hard gel to give a gelatinous functional food.

Example 14

Preparation of Plant Sterols-Containing Wheat Flour Extract

The wheat flour extract (3.0 g) obtained in Comparative Example 1 and 0.21 g of Phytosterol F were kneaded at 50° C. for 5 minutes to obtain an ocherous paste. The paste was put into 300 ml of water together with 1.5 g of decaglycerol monostearate (SY Glyster MSW-750, available from Sakamoto Yakuhin Kogyo Co., Ltd.). The mixture was treated in the same manner as in Example 10 to obtain an aqueous dispersion containing sphingoglycolipids of wheat flour origin and plant sterols.

Example 15

Preparation of Plant Sterols-Containing Rice Bran Extract

The rice bran extract (3.0 g) obtained in Comparative Example 2 and 0.56 g of Phytosterol F were kneaded at 50° C. for 5 minutes to obtain a brown paste. The paste was put into 300 ml of water together with 1.5 g of decaglycerol monostearate (SY Glyster MSW-750, available from Sakamoto Yakuhin Kogyo Co., Ltd.). The mixture was treated in the same manner as in Example 10 to obtain an aqueous dispersion containing sphingoglycolipids of rice bran origin and plant sterols.

Comparative Examples 5 to 7

For comparison, an aqueous dispersion containing sphingoglycolipids of konjac tobiko powder origin was prepared in the same manner as in Example 10, except that β-sitosterol was not added (Comparative Example 5). In 500 g of water was dispersed 2.0 g of Phytosterol F with the aid of 2.5 g of decaglycerol monostearate (SY Glyster MSW-750, available from Sakamoto Yakuhin Kogyo Co., Ltd.) as an emulsifier to prepare an aqueous dispersion (Comparative Example 6). An aqueous solution of 2.5 g of the same decaglycerol monostearate in 500 g of water was prepared (Comparative Example 7).

Test Example 3

Influences on SC Water Content

Ten volunteers for each sex (five persons between the ages of 20 and 40 and five persons between the ages of 40 and 60 for each sex) were asked to take a prescribed amount of each functional food obtained in Examples for 30 days each. The SC water content of the skin 1 cm below the left eye was measured with Corneometer after 10 days, 20 days and 30 days. The functional foods and intakes used in the test are shown in Table 3.

The average results of the twenty test persons are shown in Table 3. Table 3 proves that taking the functional foods comprising the sphingoglycolipids of konjac origin and plant sterols produces excellent effects in improving the skin SC water content.

TABLE 3

| | Daily Intake | | | SC Water Content | | | |
|---|---|---|---|---|---|---|---|
| | Food | Sphingo-glycolipids | Plant Sterols | Initial Value | After 10 Days | After 20 Days | After 30 Days |
| Example 10 | aqueous dispersion 1.45 ml | konjac 1 mg | Phytosterol F 5.8 mg | 40 | 57 | 69 | 72 |
| Example 11 | aqueous dispersion 1.45 ml | konjac 0.2 mg | Phytosterol F 5.8 mg | 43 | 58 | 66 | 69 |
| Example 12 | aqueous dispersion 1.45 ml | konjac 1.0 mg | β-sitostanol 5.8 mg | 39 | 63 | 70 | 73 |
| Example 14 | aqueous dispersion 8.33 ml | wheat 1.0 mg | Phytosterol F 5.8 mg | 42 | 56 | 61 | 64 |
| Example 15 | aqueous dispersion 3.13 ml | rice bran 1.0 mg | Phytosterol F 5.8 mg | 40 | 55 | 63 | 66 |
| Compara. Example 5 | aqueous dispersion 1.45 ml | konjac 1.0 mg | — | 41 | 55 | 60 | 63 |
| Compara. Example 6 | aqueous dispersion 1.45 ml | — | Phytosterol F 5.8 mg | 39 | 42 | 43 | 45 |
| Compara. Example 7 | solution 1.45 ml | — | — | 38 | 39 | 43 | 40 |

Phytosterol F: Plant sterols of soybean oil origin mainly comprising β-sitosterol, available from Eisai Co., Ltd.

Test Example 4

Skin Roughening Improving Effects

Cooperation of ten females suffering from skin roughening on the back of their hands was obtained. The test persons were asked to daily take in a prescribed amount of each functional food prepared in Examples for 15 days. Meanwhile they were asked to answer a questionnaire about the condition of the back of their hands after 5 days, 10 days and 15 days. The samples and intakes used are shown in Table 4.

The results obtained are shown in Table 4 as a total score. It is seen from Table 4 that taking functional foods comprising the sphingoglycolipids of konjac origin and plant sterols produces excellent improving effects on skin roughening.

TABLE 4

| | Daily Intake | | | Skin Roughening Improving Effects | | |
|---|---|---|---|---|---|---|
| | Food | Sphingo-glycolipids | Plant Sterols | After 5 Days | After 10 Days | After 15 Days |
| Example 10 | aqueous dispersion 1.45 ml | konjac 1 mg | Phytosterol F 5.8 mg | 27 | 30 | 35 |
| Example 11 | aqueous dispersion 1.45 ml | konjac 0.2 mg | Phytosterol F 5.8 mg | 22 | 28 | 32 |
| Example 12 | aqueous dispersion 1.45 ml | konjac 1.0 mg | β-sitostanol 5.8 mg | 25 | 30 | 36 |
| Example 14 | aqueous dispersion 8.33 ml | wheat 1.0 mg | Phytosterol F 5.8 mg | 23 | 25 | 28 |
| Example 15 | aqueous dispersion 3.13 ml | rice bran 1.0 mg | Phytosterol F 5.8 mg | 25 | 28 | 30 |
| Compara. Example 5 | aqueous dispersion 1.45 ml | konjac 1.0 mg | — | 20 | 24 | 26 |
| Compara. Example 6 | aqueous dispersion 1.45 ml | — | Phytosterol F 5.8 mg | 10 | 13 | 16 |
| Compara. Example 7 | solution 1.45 ml | — | — | 8 | 12 | 14 |

Phytosterol F: Plant sterols of soybean oil origin mainly comprising β-sitosterol, available from Eisai Co., Ltd.

Answers and Scores:
 4 . . . The skin roughening was completely healed.
 3 . . . The skin condition was improved greatly.
 2 . . . The skin condition was improved.
 1 . . . The skin condition was unchanged.
 0 . . . The skin condition got worse.

Example 16

Preparation of Cosmetic Containing Sphingoglycolipids of Konjac Origin

An ethyl acetate:methanol (=9:1; 200 ml) mixed solvent was passed through a column packed with 150 ml of silica gel (Silica Gel 60, available from Nacalai tesque, Inc.; 70 to 230 mesh). When the solvent liquid level reached the upper edge of silica gel, and effusion became slow, 1.9 g of precipitate A of Example 4 dissolved in hexane to make 6.0 ml was introduced into the column. Then 400 ml of an ethyl acetate:methanol (=9:1) mixed solvent was passed through, and the effluent was collected in 20 ml fractions. Each fraction was analyzed by thin layer chromatography. The 12th to 17th fractions developed deep spots of sphingoglycolipids. The fractions in this range were combined, and the solvent was removed by evaporation to give 386 mg of a solid. HPLC revealed that the sphingoglycolipids content of the solid was 226 mg, indicating that the resulting sphingoglycolipids-containing product had a sphingoglycolipids concentration of 58.5 wt %.

An ethyl acetate:methanol (=95:5) mixed solvent (200 ml) was passed through a column packed with 150 ml of silica gel (Silica Gel 60, available from Nacalai tesque, Inc.; 70 to 230 mesh). When the solvent liquid level reached the upper edge of silica gel, and effusion became slow, 386 mg of the solid prepared above by silica gel column chromatography and dissolved in a small amount of hexane was introduced into the column. Then 800 ml of an ethyl acetate:methanol (=95:5) mixed solvent was passed through, and the effluent was collected in 20 ml fractions. Each fraction was analyzed by thin layer chromatography. A single spot of sphingoglycolipids was observed with the 20th to 26th fractions. The fractions in this range were combined, and the solvent was removed by evaporation to give 87 mg of a solid. HPLC revealed that the sphingoglycolipids content of the solid was 86 mg, indicating that the resulting sphingoglycolipids-containing product had a sphingoglycolipids concentration of 98.9 wt %.

The solid (50.6 mg) was put into 10 ml of water with stirring and dispersed by ultrasonication using BRANSON 3200, available from Yamato Scientific Co., Ltd., for 30 minutes to obtain a cosmetic containing sphingoglycolipids of konjac tobiko powder origin according to the present invention. The resulting sphingoglycolipids-containing aqueous dispersion was uniform and produced no sediment when allowed to stand for one day. This aqueous dispersion contained 50 mg of sphingoglycolipids of konjac tobiko powder origin.

Example 17

Preparation of Cosmetic Containing Sphingoglycolipids of Potato Origin

Five grams of the potato peel extract obtained in Example 3 was dissolved in 10.0 g of ethanol, and the solution was introduced into 100 g of water while stirring. The mixture was further stirred while in a dispersed state. Thirty minutes later, 2.5 g of sodium chloride was added, and the stirring was continued for additional 10 minutes to give a light brown precipitate, which weighed 3.0 g. The sphingoglycolipids content was 0.18 g as measured by HPLC. After washing with water, the extract had a sphingoglycolipids purity of 6.0 wt %. The washing operation was repeated once more to give 2.8 g of a precipitate, which was found to have a sphingoglycolipids content of 0.18 g as a result of HPLC. The purity of the sphingoglycolipids obtained after washing twice was 6.4 wt %. The resulting product containing sphingoglycolipids of potato peel origin was purified twice by silica gel column chromatography in the same manner as in Example 16 to obtain 38 mg of a sphingoglycolipids-containing product having a sphingoglycolipids content of 96.8 wt %.

The above-described series of operations were repeated several times. The thus produced product containing sphingoglycolipids of potato peel origin (51.7 mg) was put into 10 ml of water while stirring and dispersed by 30-minute ultrasonication by use of BRANSON 3200, available from Yamato Scientific Co., Ltd., to obtain a cosmetic containing the sphingoglycolipids of potato peel origin according to the present invention. The resulting sphingoglycolipids-containing aqueous dispersion was uniform and generated no sediment after one-day standing. This aqueous dispersion contained 50 mg of sphingoglycolipids of potato peel origin.

Comparative Example 8

Preparation of Cosmetic Containing Sphingoglycolipids of Wheat Origin

Five grams of the wheat flour extract obtained in Comparative Example 1 was dissolved in 10.0 g of ethanol, and the solution was introduced into 100 g of water while stirring. The mixture was further stirred while in a dispersed state. Thirty minutes later, 2.5 g of sodium chloride was added, and the stirring was continued for 10 minutes to give a brown precipitate, which weighed 3.6 g. The sphingoglycolipids content was 0.04 g as measured by HPLC. After washing with water, the extract had a sphingoglycolipids purity of 1.1 wt %. The washing operation was repeated once more to give 3.4 g of a precipitate, which was found to have a sphingoglycolipids content of 0.04 g as a result of HPLC. The purity of the sphingoglycolipids obtained after washing twice was 1.2 wt %. The resulting product containing sphingoglycolipids of wheat origin was purified twice by silica gel column chromatography in the same manner as in Example 16 to obtain 2 mg of a sphingoglycolipids-containing product having a sphingoglycolipids content of 97.5 wt %.

The above-described series of operations were repeated several times. The thus produced product containing sphingoglycolipids of wheat origin (51.3 mg) was put into 10 ml of water while stirring and dispersed by 30-minute ultrasonication by use of BRANSON 3200, available from Yamato Scientific Co., Ltd. The resulting sphingoglycolipids-containing aqueous dispersion was uniform and generated no sediment after one-day standing. This aqueous dispersion contained 50 mg of sphingoglycolipids of wheat origin.

Comparative Example 9

Preparation of Cosmetic Containing Sphingoglycolipids of Rice Bran Origin

Ten grams of the defatted rice bran extract obtained in Comparative Example 2 was dissolved in 20.0 g of ethanol, and the solution was introduced into 200 g of water while stirring. The mixture was further stirred while in a dispersed state. Thirty minutes later, 5.0 g of sodium chloride was added, and the stirring was continued for 10 minutes to form a brown precipitate, which weighed 7.4 g. The sphingoglycolipids content of the precipitate was 0.24 g as measured by HPLC. After washing with water, the extract had a sphingoglycolipids purity of 3.2 wt %. The washing operation was repeated once more to give 6.9 g of a precipitate, which was found to have a sphingoglycolipids content of 0.22 g as a result of HPLC. The purity of the sphingoglycolipids obtained after washing twice was 3.2 wt %. The resulting product containing sphingoglycolipids of rice bran origin was purified twice by silica gel column chromatography in the same manner as in Example 16 to obtain 28 mg of a sphingoglycolipids-containing product having a sphingoglycolipids content of 98.2 wt %.

The above-described series of operations were repeated several times. The thus produced product containing sphingoglycolipids of rice bran origin (50.9 mg) was put into 10 ml of water while stirring and dispersed by 30-minute ultrasonication by use of BRANSON 3200, available from Yamato Scientific Co., Ltd. The resulting sphingoglycolipids-containing aqueous dispersion was uniform and generated no sediment after one-day standing. This aqueous dispersion contained 50 mg of sphingoglycolipids of rice bran origin.

Test Example 5

Influences on SC Water Content

The skin SC water content improving effects of the cosmetics of the invention obtained in Examples 16 and 17 and the aqueous dispersions obtained in Comparative Examples 8 and 9 were tested with cooperation of ten female volunteers suffering from dry skin (five persons between the ages of 20 and 40 and five persons between the ages of 40 and 60). The test persons were asked to apply 0.5 ml of each aqueous dispersion on the inner side of the left upper arm for consecutive 30 days each. The skin SC water content of the inner side of the left upper arm was measured with Corneometer after 10 days, 20 days and 30 days. The results obtained are shown in Table 5 together with the results of control (the skin where the dispersion was not applied).

TABLE 5

|  | Initial Value | After 10 Days | After 20 Days | After 30 Days |
| --- | --- | --- | --- | --- |
| Example 16 (tobiko powder origin) | 47 | 65 | 75 | 78 |
| Example 17 (potato origin) | 48 | 63 | 71 | 73 |
| Compara. Example 8 (wheat flour origin) | 48 | 58 | 60 | 60 |
| Compara. Example 9 (rice bran origin) | 45 | 58 | 62 | 64 |
| Control (no application) | 49 | 45 | 47 | 46 |

It can be seen from Table 5 that applying sphingoglycolipids of konjac tobiko powder origin or potato peel origin produces excellent effects of improving SC water content of the skin.

Example 18 and Comparative Example 10

Preparation of Sphingoglycolipids-Containing Beauty Lotion

A beauty lotion containing sphingoglycolipids of konjac tobiko powder origin was prepared according to the formulation shown in Table 6 below (Example 18). A beauty lotion was prepared according to the same formulation except for the sphingoglycolipids (Comparative Example 10).

TABLE 6

| | |
|---|---|
| Sphingoglycolipids-containing product of Example 16 (sphingoglycolipids concentration: 98.9%) | 0.5 wt % |
| Propylene glycol | 4.0 wt % |
| 70% Sorbitol solution | 3.0 wt % |
| Ethanol | 5.0 wt % |
| Perfume | 0.1 wt % |
| Methyl p-hydroxybenzoate | 0.1 wt % |
| Sodium citrate | 0.2 wt % |
| Purified water | balance |

Test Example 6

Improvement on Feel of Use

The beauty lotions obtained in Example 18 and Comparative Example 10 were organoleptically tested by twenty females for evaluating the feel on application for 2 months. The results are shown in Table 7.

TABLE 7

| | Duration of feel of moisture | Make-up Wear-ability | Make-up Dura-bility | Skin Elas-ticity | Skin Flexi-bility | Overall Judge-ment |
|---|---|---|---|---|---|---|
| Example 18 | 37 | 30 | 32 | 35 | 37 | 38 |
| Compara. Example 10 | 28 | 28 | 31 | 26 | 26 | 27 |

Answers to Questionnaire and Scores:
2 . . . Considerably good
1 . . . Slightly good
0 . . . Not good The figures in Table 7 are total scores.

It is seen from Table 7 that the beauty lotion containing sphingoglycolipids of konjac tobiko powder origin exhibits excellent effects in duration of moisture feel, skin elasticity and skin flexibility.

INDUSTRIAL APPLICABILITY

The sphingoglycolipids-containing functional foods and cosmetics according to the present invention contain sphingoglycolipids, which exist in human skin and seem to play an important role in moisture retention, in a high concentration and produce excellent effects in improving the SC water content of human skin and improving rough skin, atopic dermatitis, allergic dermatitis, pimples, and so forth. According to the production method according to the invention, sphingoglycolipids-containing functional foods and cosmetics can be produced easily and economically by using as raw materials konjac tobiko powder, potato peel, oil cakes, etc. that have not been utilized as food at all.

While the invention has been described in detail and with reference to specific examples thereof, it will be apparent to one skilled in the art that various changes and modifications can be made therein without departing from the spirit and scope thereof.

This application is based on Japanese Patent Application Nos. 2000-219087 filed Jul. 19, 2000, 2001-021947 filed Jan. 30, 2001, 2001-087695 filed Mar. 26, 2001, and 2001-188393 filed Jun. 21, 2001, which are incorporated herein by reference.

What is claimed is:

1. A functional food comprising a sphingoglycolipid derived from a tuberous and corm vegetable or cotton seed oil cake.

2. A functional food comprising a sphingoglycolipid derived from a tuberous and corm vegetable or cotton seed oil cake and a plant sterol.

3. A functional food according to claim 2, wherein said sphingoglycolipid is extracted from a tuberous and corm vegetable or cotton seed oil cake.

4. A functional food according to claim 1 or 3, wherein the tuberous and corm vegetable is konjac.

5. A cosmetic comprising a sphingoglycolipid derived from a tuberous and corm vegetable or cotton seed oil cake.

6. A cosmetic according to claim 5, wherein the tuberous and corm vegetable is konjac.

7. A method of producing a functional food or a cosmetic according to any one of claims 1, 3, 5 or 6, which comprises the steps of adding an organic solvent to a tuberous and corm vegetable or cotton seed oil cake and extracting a sphingoglycolipid.

8. A method of producing a sphingoglycolipid-containing product, which comprises the steps of adding an organic solvent to a tuberous and corm vegetable or cotton seed oil cake and extracting a sphingoglycolipid.

9. A method for producing a functional food according to claim 4 which comprises the steps of adding an organic solvent to a tuberous and corm vegetable or cotton seed oil cake and extracting a sphingoglycolipid.

* * * * *